United States Patent
Tepic et al.

(10) Patent No.: US 6,309,393 B1
(45) Date of Patent: *Oct. 30, 2001

(54) BONE PLATE

(75) Inventors: Slobodan Tepic, Zurich; Stephen J. Bresina; Stephen Perren, both of Davos Dorf, all of (CH)

(73) Assignee: Synthes (U.S.A.), Paoli, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,134

(22) PCT Filed: Aug. 12, 1996

(86) PCT No.: PCT/CH96/00278

§ 371 Date: Feb. 10, 1999

§ 102(e) Date: Feb. 10, 1999

(87) PCT Pub. No.: WO98/06345

PCT Pub. Date: Feb. 19, 1998

(51) Int. Cl.$^7$ .................................................. A61B 17/80
(52) U.S. Cl. ............................................................ 606/69
(58) Field of Search .............................. 606/60, 61, 69, 606/70, 71

(56) References Cited

U.S. PATENT DOCUMENTS

| | | | |
|---|---|---|---|
| 5,053,036 | * | 10/1991 | Perren et al. ........................... 606/69 |
| 5,549,612 | * | 8/1996 | Yapp et al. ............................. 606/69 |
| 5,733,287 | * | 3/1998 | Tepic et al. ............................ 606/69 |
| 5,807,396 | * | 9/1998 | Raveh .................................... 606/69 |

FOREIGN PATENT DOCUMENTS

| | | |
|---|---|---|
| 0 355 035 B1 | 2/1990 | (EP) . |
| 0 530 585 A2 | 3/1993 | (EP) . |
| 0 684 017 A1 | 11/1995 | (EP) . |

\* cited by examiner

*Primary Examiner*—David O. Reip
(74) *Attorney, Agent, or Firm*—Pennie & Edmonds LLP

(57) ABSTRACT

The present invention relates to a bone plate having a top side, a bottom side for contacting the bone, two longitudinal sides, a plurality of holes which extend from the top side to the bottom side, and a longitudinal axis. The cross-section of the holes tapers from the top side to the bottom side and the bottom side is provided with recesses. The surface of the top side adjacent to the holes forms island-like recesses relative to the remaining surface of the top side. The bottom side is provided with two different types of recesses which create a plurality of supporting points for contacting the bone. In addition, the holes conically taper from the top side to the bottom side.

18 Claims, 2 Drawing Sheets

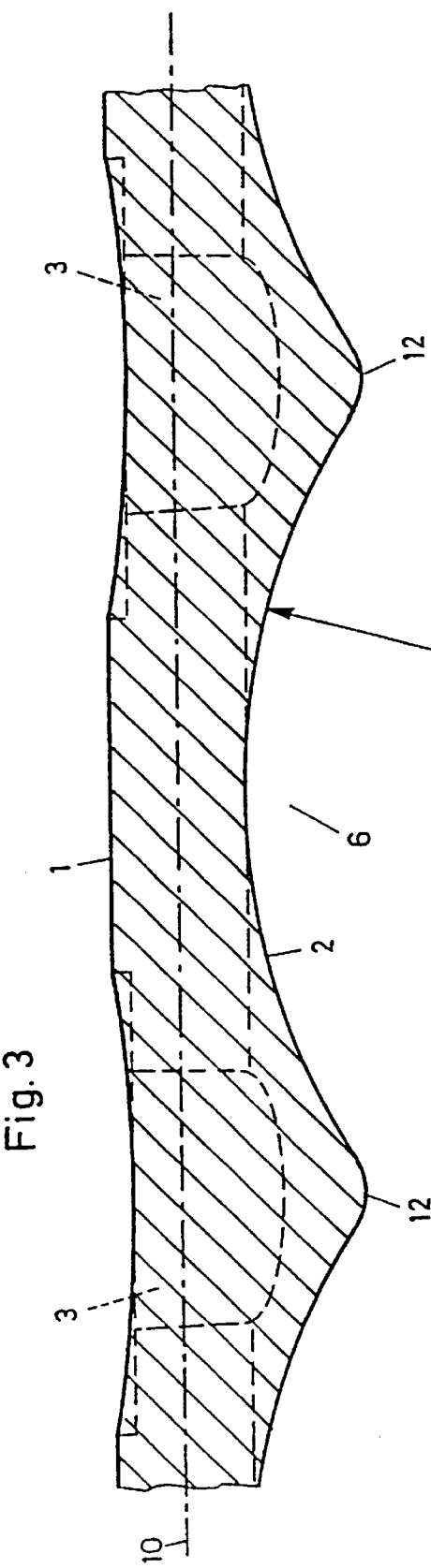
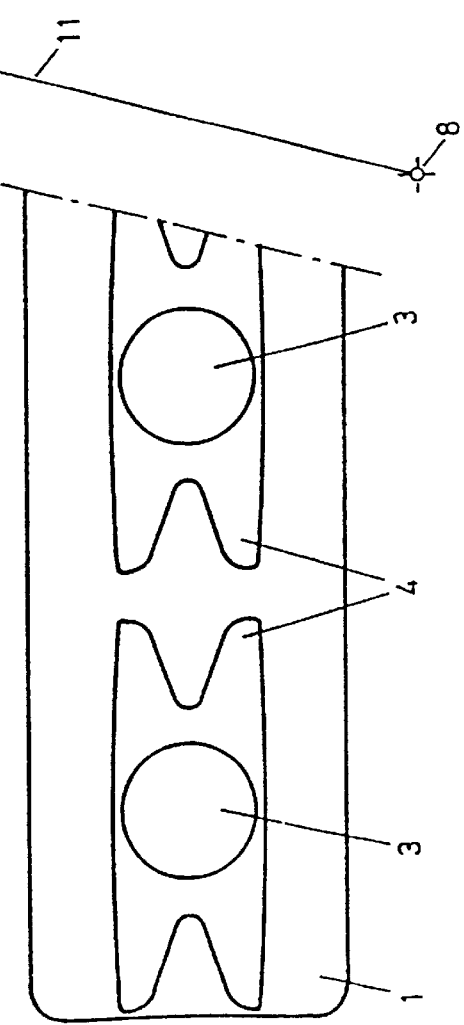

BONE PLATE

FIELD OF THE INVENTION

The present invention relates generally to a bone fixation device, and in particular to a bone plate.

BACKGROUND OF THE INVENTION

Bone plates have been used for many years in the field of orthopaedics. There have been many attempts to develop improved bone plates. For example, European Patent No. B 0355 035 teaches a bone plate with conical plate holes which provide a rigid connection between the plate and the fixation screws even after bone resorption has occurred. The plate disclosed in this European Patent has a concave bone-contacting surface which reduces the surface area of bone contact in order to improve the healing process. Published European Patent Application A 0 684 017 discloses a bone plate having widened plate holes on the upper side. Despite these and other advancements, all known bone plates have drawbacks. For example, common concerns related to the use of bone plates include strength of the implant, stability of fixation on the bone, and biological incorporation.

Thus, there exists a need for an improved bone plate.

SUMMARY OF THE INVENTION

One object of the present invention is to create a bone plate that, in addition to optimum incorporation characteristics, has the lowest possible volume (and therefore weight) while still having a high degree of strength.

Compared to the prior art, the bone plate according to the present invention has the following advantages:

- Optimum utilization of material characteristics through optimum distribution of tension when bending the bone plate, inserting the bone screws, and transferring the load in the implanted state;
- Optimum bearing surface on the bone;
- Optimum bearing force of the bone plate on the bone, which guarantees minimal disruption of blood supply;
- Blocking of the conical screw heads in the conical screw hole, which means that the transfer of force in the bone/plate bond is no longer based on friction, but instead forms a positive-locking system.

The bone plate according to the present invention has an upper side, a lower side with a plurality of projections between first and second recesses configured and dimensioned to produce a plurality of bearing surfaces for contact with bone, at least two sides arranged about a longitudinal axis of the plate, and at least one plate hole extending from the upper side to the lower side of the plate for receiving a fastener. The upper side includes a region adjacent each plate hole with an insular recess.

In order to promote load transfer, the plate holes may taper conically from the upper side to the lower side with a cone angle from about 5° to 7°. Preferably, the fastener is a bone screw having a conical head. At least part of the bone screw surface may be anodized to prevent the screw head from sticking in the plate hole.

In one embodiment, the first recesses include a first cylindrical recess having a longitudinal axis oriented parallel to the longitudinal axis of the bone plate. Each second recess may include a second cylindrical recess with the longitudinal axis running between plate holes and either perpendicular or oblique to the longitudinal axis of the bone plate. The radius of the first cylindrical recess is preferably from about 3.2 mm to 3.8 mm and the radius of the second cylindrical recess is preferably from about 9 mm to 15 mm.

Although the dimensions of the bone plate will vary with application, the width is preferably from about 8 mm to 11 mm and the thickness is preferably from about 1.9 mm to 2.8 mm. Furthermore, the longitudinal sides of the plate may converge toward the lower side to minimize the degree of bone coverage by the plate.

With respect to the insular recess, the bone plate preferably has insular recesses with a volume of at least 20 mm$^3$ but less than 50 mm$^3$ and a surface area from about 38 mm$^2$ to 47 mm$^2$. The surface area of each insular recess may be from about 2.5 times to 4.2 times larger than the surface area of each plate hole. The insular recess may have a butterfly-like shape with swallowtails. Preferably, the swallowtails are parallel to the longitudinal axis of the bone plate.

The invention and developments of the invention are described in greater detail below using partially schematic illustrations of several embodiments in which:

FIG. 3 shows a partial longitudinal section through the bone plate in accordance with the invention as shown in FIG. 1.

FIG. 4 shows a top view of a modified bone plate in accordance with the invention.

DETAILED DESCRIPTION OF THE PREFERRED EMBODIMENTS

Figure 1:
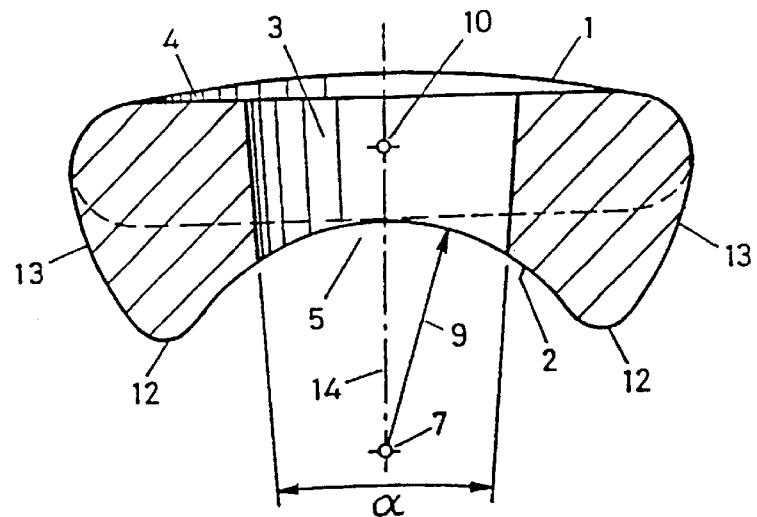
FIG. 1 shows a cross section through the bone plate in accordance with the invention.
Figure 2:
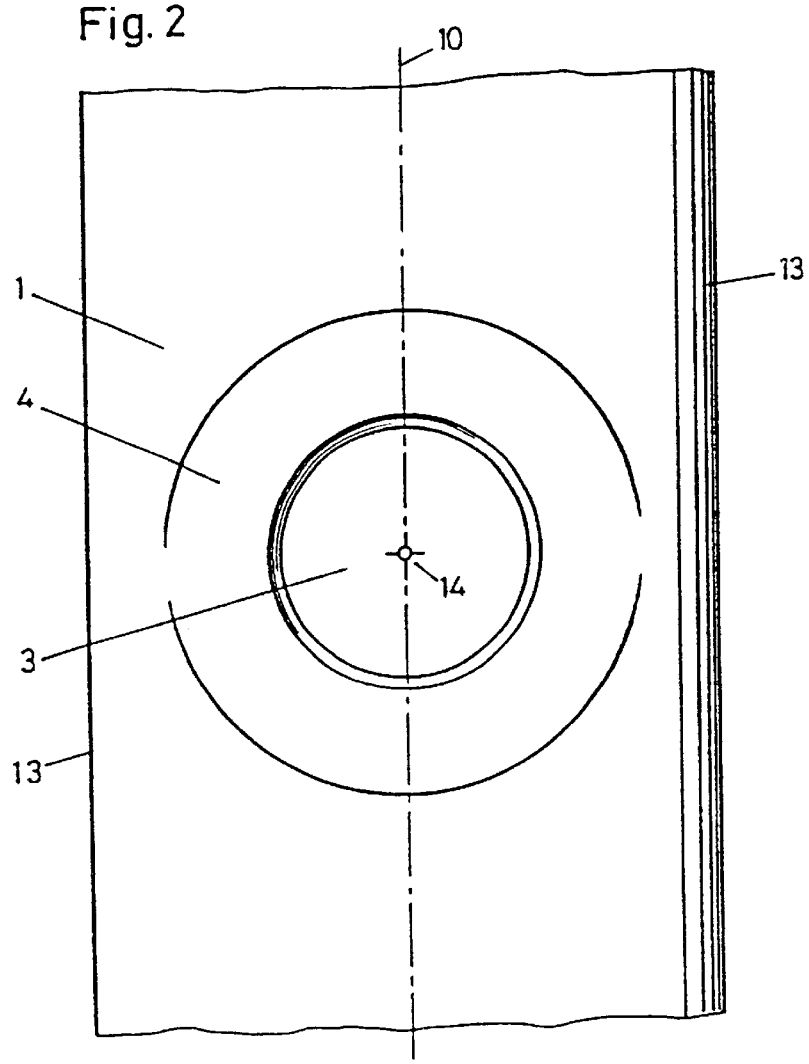
FIG. 2 shows a partial top view of the bone plate in accordance with the invention as shown in FIG. 1.

The bone plate shown in FIGS. 1 through 3 comprises substantially an upper side 1, a lower side 2 intended for contact with the bone, two longitudinal sides 13, a number of plate holes 3 that extend from upper side 1 to lower side 2, and a longitudinal axis 10.

As shown in FIG. 1, the cross section of plate holes 3 tapers conically from upper side 1 toward lower side 2, and cone angle α is 5.72°. The largest cross-sectional area of plate hole 3 is 12.8 mm$^2$.

The surface of upper side 1 adjacent to plate holes 3 has an insular recess 4 compared with the remaining surface of upper side 1. Insular recess 4 has a total surface area, including the surface area of plate hole 3 surrounded by it, of 42.8 mm$^2$.

Instead of the circular design shown in FIG. 2, insular recess 4 on upper side 1 of the bone plate (as shown in FIG. 4) can also be in the shape of a butterfly with two swallowtails running in the direction of longitudinal axis 10. Surprisingly, it has been shown that this design of insular recess 4 provides particularly good mechanical strength of the plate (moreover at the same weight).

Lower side 2 of the bone plate is (as shown in FIGS. 1 and 3) provided with two different types of recesses 5; 6, which form a multiplicity of bearing points 12 intended for contact with the bone. The bearing points can be more or less truncated; the important thing is the reduction in total bone bearing surface of the bone plate that they provide. Recesses 5; 6 in lower side 2 of the bone plate comprise on the one hand a first cylindrical recess 5, with cylinder axis 7 of first cylindrical recess 5 running parallel to longitudinal axis 10, and on the other hand a multiplicity of second cylindrical recesses 6, with cylinder axes 8 of second cylindrical recesses 6 running between individual plate holes 3 and perpendicular to longitudinal axis 10.

Radius 9 of first cylindrical recess 5 is approximately 3.5 mm, and radius 11 of second cylindrical recess 6 is approximately 15 mm.

The width of the bone plate is 9.5 mm, and its minimum thickness is 2.2 mm. The distance between individual plate holes 3 is 13 mm.

Insular recess 4 has a total surface area, including the surface area of plate hole 3 surrounded by it, of approximately 38 to 47 mm², preferably from 41 to 44 mm. It is advantageous for insular recess 4 to have a total surface area F, including surface area f of plate hole 3 surrounded by it, of 2.5 f<F<4.2 f, preferably from 3.0 f<F<3.6 f.

The volume of insular recesses 4, including their area in the plate hole, is advantageously at least 20 mm³, preferably at least 25 mm³, and is advantageously a maximum of 50 mm³, preferably a maximum of 40 mm³, in size.

What is claimed is:

1. A bone plate comprising:
   an upper side;
   a lower side having a plurality of projections formed by first and second recesses configured and dimensioned to produce a plurality of bearing surfaces for contact with bone;
   at least two lateral sides arranged about a longitudinal axis of the plate; and
   at least one plate hole extending from the upper side to the lower side of the plate for receiving a fastener,
   wherein the upper side includes a region adjacent the at least one plate hole with an insular recess, and wherein each of the plurality of projections intersects one lateral side.

2. The bone plate of claim 1 wherein the lateral sides of the plate converge toward the lower side.

3. The bone plate of claim 1 wherein the bone plate has a width from about 8 mm to 11 mm.

4. The bone plate of claim 1 wherein the bone plate has a thickness from about 1.9 mm to 2.8 mm.

5. The bone plate of claim 1 wherein the insular recess has a volume of at least 20 mm³ but less than 50 mm³.

6. The bone plate of claim 1 wherein the insular recess has a surface area from about 38 mm² to 47 mm².

7. The bone plate of claim 1 wherein the insular recess has a surface area that is from about 2.5 times to 4.2 times larger than the surface area of each plate hole.

8. The bone plate of claim 1 wherein the insular recess has a butterfly-like shape with swallowtails.

9. The bone plate of claim 8 wherein the swallowtails are parallel to the longitudinal axis of the bone plate.

10. A bone plate comprising:
    an upper side;
    a lower side having a plurality of projections formed by first and second recesses configured and dimensioned to produce a plurality of bearing surfaces for contact with bone;
    at least two lateral sides arranged about a longitudinal axis of the plate; and
    at least one plate hole extending from the upper side to the lower side of the plate for receiving a fastener,
    wherein the upper side includes a region adjacent the at least one plate hole with an insular recess, and wherein the at least one plate hole tapers conically from the upper side to the lower side.

11. The bone plate of claim 10 wherein the conical taper of the at least one plate hole has a cone angle from about 5° to 7°.

12. The bone plate of claim 10 wherein the fastener is a bone screw having a conical head.

13. The bone plate of claim 12 wherein at least part of the bone screw surface is anodized.

14. A bone plate comprising:
    an upper side;
    a lower side having a plurality of projections formed by first and second recesses configured and dimensioned to produce a plurality of bearing surfaces for contact with bone;
    at least two lateral sides arranged about a longitudinal axis of the plate; and
    at least one plate hole extending from the upper side to the lower side of the plate for receiving a fastener,
    wherein the upper side includes a region adjacent the at least one plate hole with an insular recess, and wherein each first recess includes a first cylindrical recess having a longitudinal axis oriented parallel to the longitudinal axis of the bone plate.

15. The bone plate of claim 14 wherein the bone plate includes at least two plate holes and each second recess includes a second cylindrical recess with the longitudinal axis running between plate holes and perpendicular to the longitudinal axis of the bone plate.

16. The bone plate of claim 15 wherein the radius of the second cylindrical recess is from about 9 mm to 15 mm.

17. The bone plate of claim 14 wherein the bone plate includes at least two plate holes and each second recess includes a second cylindrical recess having a longitudinal axis oriented between the plate hole and oblique to the longitudinal axis of the bone plate.

18. The bone plate of claim 14 wherein the radius of the first cylindrical recess is from about 3.2 mm to 3.8 mm.

* * * * *